(12) United States Patent
Glenn, Jr. et al.

(10) Patent No.: US 6,991,781 B2
(45) Date of Patent: *Jan. 31, 2006

(54) DELIVERY OF REACTIVE AGENTS VIA BI-LAYER STRUCTURES FOR USE IN SHELF-STABLE PRODUCTS

(75) Inventors: Robert Wayne Glenn, Jr., Virginia Water (GB); George Endel Deckner, Cincinnati, OH (US); Andrew James Caie, Aldershot (GB)

(73) Assignee: The Procter & Gamble Company, Cincinnati, OH (US)

( * ) Notice: Subject to any disclaimer, the term of this patent is extended or adjusted under 35 U.S.C. 154(b) by 333 days.

This patent is subject to a terminal disclaimer.

(21) Appl. No.: 09/764,560

(22) Filed: Jan. 17, 2001

(65) Prior Publication Data

US 2002/0131944 A1 Sep. 19, 2002

(51) Int. Cl.
*A61K 7/06* (2006.01)

(52) U.S. Cl. ............... 424/70.1; 424/70.11; 424/70.12; 424/70.27; 424/70.31; 424/62; 424/450

(58) Field of Classification Search ............... 424/450, 424/70.1, 70.11, 70.12, 62, 70.27, 70.31; 8/409

See application file for complete search history.

(56) References Cited

U.S. PATENT DOCUMENTS

| 5,087,733 | A | * | 2/1992 | Deppert et al. |
| 5,362,494 | A | * | 11/1994 | Zysman et al. ............. 424/401 |
| 5,525,332 | A | * | 6/1996 | Gough et al. |
| 6,544,499 | B1 | * | 4/2003 | Glenn et al. ............... 424/70.1 |
| 6,703,007 | B2 | * | 3/2004 | Glenn, Jr. .................. 424/70.1 |

* cited by examiner

*Primary Examiner*—Thurman K. Page
*Assistant Examiner*—Lakshmi Channavajjala
(74) *Attorney, Agent, or Firm*—Linda M. Sivik; Brahm J. Corstanje; Tera M. Rosnell

(57) ABSTRACT

Disclosed are treatment composition, comprising an aqueous continuous phase; a reactive component comprising a reactive agent and a water immiscible solvent, wherein the water immiscible solvent solubilizes the reactive agent; and one or more surfactants wherein the surfactants emulsify the reactive component in the aqueous phase to form a bi-layer emulsion. Also disclosed are methods for treating amino acid based substrates, and methods for bleaching, coloring and conditioning hair with these treatment compositions.

21 Claims, No Drawings

US 6,991,781 B2

DELIVERY OF REACTIVE AGENTS VIA BI-LAYER STRUCTURES FOR USE IN SHELF-STABLE PRODUCTS

FIELD OF INVENTION

The present invention relates to a system for the delivery of reactive cosmetic actives (such as reactive conditioners, dyes, styling aids, sunscreens etc.) to amino acid based substrates from a chemically shelf stable formulation.

BACKGROUND OF THE INVENTION

Consumers have been treating amino acid based substrate for years. Such treatments have included the waterproofing or coloring of textiles, the sunscreening of skin, the coloring, conditioning, and styling of hair, the dentifirce treatment of teeth, and more. It is well known that if such treatment can be done by some kind of safe covalent attachment to the substrate, that the treatment will be much more long lasting. Therefore, several reactive chemistries have been developed to provide covalent attachment to amino acid based substrates such as hair. Historically, these technologies, based on covalent attachment of cosmetic actives, have primarily relied upon electrophilic (electron accepting) and nucleophilic (electron donating) reactive groups or "hooks". More recently, a Protected Thiols "hook" technology for the covalent attachment of cosmetic actives to amino acid substrates has been proposed.

It is highly desirable to formulate consumer products as aqueous solutions or aqueous emulsions for a number of consumer preferred attributes, e.g., ease of rinsing, aesthetic feel, less coating of bathroom tiles, environmental concerns, etc. However, attaining such aqueous compositions is problematic in the delivery of technologies for the covalent attachment of cosmetic actives to amino acid based substrates. The reactive groups or "hook" moieties which are reactive towards amino acid residues in hair protein are also reactive towards electron rich ingredients that are employed in the formulation of consumer products to deliver these actives, including water and even atmospheric oxygen. This leads to pre-mature decomposition of the hooks of covalent reactive compounds, referred to herein as reactive agents, over the shelf life of the product which severely or completely mitigates reactive efficacy with a substrate upon usage by the consumer.

The primary advantage of the present invention is the discovery of a delivery system approach that will enable the formulation and delivery of reactive agents to amino acid based substrates from an aqueous composition that is chemically shelf stable. This is accomplished via a delivery system wherein the reactive agent is solubilized within a suitable water immiscible solvent and then the solvent is emulsified within the aqueous phase into structured bi-layer phases, or bi-layers, which confers improved chemical shelf stability to the reactive agent. While not being bound to theory, it is believed that the water immiscible solvent comprising the reactive agent serves as a diffusion barrier that minimizes contact between the chemically unstable reactive agent and the aqueous phase. The structured bi-layers surrounding the water immiscible solvent are a further barrier between the reactive agent and the aqueous phase. The bi-layers also serve to keep the reactive agent dispersed within the aqueous continuous phase over the shelf life of the composition to enable the delivery of the reactive agent to the hair in a consumer preferable medium, i.e., an aqueous emulsion cream, and without additional consumer inconvenience.

Furthermore, on occasions wherein the reactive agent is charged, e.g., cationic, or anionic, the bi-layers can formed of surfactants with the same net charge of the reactive agent which acts as an even further barrier between the reactive agent and the aqueous phase via coulombic repulsive forces that repel the reactive agent from aggregating at the water/solvent interface.

SUMMARY OF THE INVENTION

This invention relates to a treatment composition, comprising an aqueous continuous phase; a reactive component comprising a reactive agent and a water immiscible solvent, wherein the water immiscible solvent solubilizes the reactive agent; and one or more surfactants wherein the surfactants emulsify the reactive component in the aqueous phase to form a bi-layer emulsion.

DETAILED DESCRIPTION OF THE INVENTION

The present invention relates to delivery of reactive agents via bi-layer structures for use in chemically shelf stable products.

The term "amino acid based substrates", as used herein, refers to proteinaceous materials, such as keratin, as found in human and animal hair, skin, and nails. Amino acid based substrates useful herein are hydroxyl-containing, amine-containing, thiol-containing, and disulfite-containing amino acids.

The term "covalently reactive", as used herein, refers to the ability of reactive agents to form covalent bonds with functional groups within proteinaceous keratin, e.g., with keratin amino acids comprising —SH, —OH, —NH$_2$ or —S—S— groups, thereby forming a permanent bond with the keratin that is resistant to shampooing or cleansing.

The term "water immiscible solvent", as used herein, refers to solvents which can solubilize the reactive agent, and which cannot be uniformly mixed or blended with water or a separate aqueous phase.

The term "reactive agent", as used herein, refers to compounds that comprise a reactive group or "hook" that is covalently reactive with keratin and a mono or multivalent cosmetically active functional group that imparts one or more visual, tactile or other cosmetic beneficial effects on proteinaceous materials such as keratin, hair, skin, animal fur or wool.

The term "chemically shelf stable" or "chemically stable", as used herein, applies to a composition comprising a reactive agent wherein the reactive agent does not chemically decompose substantially (via hydrolysis, reduction or oxidation) over the desired shelf life of the product such that the reactive agent maintains its ability to react with the proteinaceous substrate.

The treatment compositions of the present invention can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Reactive Component

The compositions of the present invention comprise a reactive component which in turn comprises a chemically unstable reactive agent and a water immiscible solvent which solubilizes the reactive agent. The reactive agent comprises a reactive group or "hook" and a mono or multivalent cosmetically active functional group that imparts one or more visual, tactile or other cosmetic beneficial effects on proteinaceous materials such as keratin, hair, skin, animal fur or wool. The reactive agent comprises one or more reactive groups selected from the group consisting of electrophilic, nucleophilic, protected thiol groups and mixtures thereof.

Disclosed technologies for the covalent attachment of cosmetic actives (primarily dyes and conditioners) to hair keratin have primarily relied upon electrophilic (electron accepting) and nucleophilic (electron donating) reactive groups or "hooks".

Electrophilic reactive groups or "hooks" that may be included within reactive agents of the present inventions include, but are not limited to, the following:

Azolactones as described in U.S. Pat. No. 5,656,265 by P. Bailey et. al., and U.S. Pat. Nos. 5,523,080 and 5,525, 332 both by A. Gough et. al., and all incorporated by reference, Alkyl halides as described in U.S. Pat. Nos. 5,211,942 and 5,030,756 by T. Deppert et. al., both incorporated by reference, Thiosulfates as described in U.S. Pat. No. 3,415,606 by R. Randebrock, and incorporated by reference, Dithiocarboxylic acid esters wherein preferred carboxyalkyl carbodithioates have the general formula:

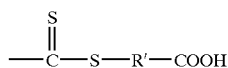

where R is an organic group and
R' is an alkylene group containing 1, 2 or 3 carbon atoms.
The group R may be:
(a) an aliphatic group, for example alkyl, which may contain far instance up to 24 carbon atoms;
(b) an aromatic group, for example phenyl or naphtyl;
(c) a mixed aliphatic-aromatic group for example alkaryl or aralkyl;
(d) a heterocyclic group, for example furyl;
(e) a quaternary ammonium-alkylene group, for example an N-pyridinium-alkylene group, Acyl halides—polyhaloacetylated polymers are essentially characterized in that they all contain a halogen (chlorine or bromine, but preferably chlorine) on a carbon in the alpha position relative to a carbonyl group. These polymers which are polyhaloacetylated and preferably polychloroacetylated, may be obtained according to different methods. In particular, they may be obtained by the homopolymerization or the copolymerization of a haloacetylated monomer carrying a polymerizable double bond; among the haloacetylated monomers, there will be mentioned, in particular, the following: vinyl chloroacetate, allyl chloroacetate, vinyl chloroformate, N-allyl chloroaceta- methyl 2-chloroacetamidoacryLate, N-chLoroacetamidomethyl acrylamide, N-chloroacetamidomethyl methacrylamide, 5 2-(chloroacetoxy)propyl methacrylate, 2-(chLoroacetylcarbamoyloxy)propyl methacrylate, N-methacryloyl-N'-chloroacetylurea and the like; in the case of a copolymerization, a comonomer which promotes the solubility of the final copolymer in the solvent desired, which is generally water or a water-alcohol mixture, is preferably chosen; among comonomers, there will be mentioned, in particular, the following N-vinylpyrrolidone, N,N-dimethylacrylamide, N-acrylamidomethyl-2-oxopyrrolidone, 3 -methacrylamidopropyl-1-(N,N,N-trimethylammonium) chloride, methylacrylate, methylmethacrylate, N,N-dimethylacrylamide and the like. The haloacetylated monomers are known and may be prepared according to known methods. The polyhaloacetylated polymers may also be obtained by attaching a haloacetyl group to a polymer carrying amine or primary or secondary alcohol groups, the haloacetyl group being attached in a known manner which consists in reacting a haloacetyl halide, preferably chloroacetyl chloride, with the said polymer carrying amine or alcohol groups; among the polymers which nay be employed for this haloacetylation reaction, there may by mentioned, in p2rticular: polyvinyl amine, polyvinyl alcohol, 2-hydroxyethyl polyacrylate, polylysine, copolymers obtained by condensing 2,2-dimethyl-1,3-diaminopropane with methylene bisacrylamide, water-soluble protein hydrolysates and the like. The polyhaloacetylated polymers employed preferably have a molecular weight generally of between 500 and 50,000. Although some of the homopolymers and copolymersare known, examples for the preparation of some of them as well as examples for the preparation of the haloacetylated monomers will be given as follows: Among the homopolymers and the polyhaloactylated-copolymers which are particularly preferred for implementing the method, the following may be mentioned: N-vinylpyrrolidone/vinyl chlchloroacetate copolymer, methyl 2-chloroacetamidoacrylate/N-acrylamido-methyl-2-oxopyrrolidine copolymer, methyl 2-chloroacetamidoacrylate homopolymer, N-chloroacetamidonethyl acrylamide/N-acrylamidomethyl-2-oxopyrrolidine copolymer, methyl 2-chloroacetamidoacrylate/methacrylamido-propyl trimethylammonium chloride copolymer, N-chloroacetamidomethyl acrylamide/methyl acrylate copolyner, N-chloroacetamidomethyL acrylamide homopolymer, and N-chloroacetamidomethyl acrylamide/methacrylamido-propyl trimethylammonium chloride copolymer, N-ethylmaleimides, Halotriazines and halopyrimidines as described in U.S. Pat. No. 3,340,000 by A. Shansky, and incorporated by reference, Vinylsulfones as manufactured by Carbic Hoechst Corporation, (451 Washington Street, New York 13, N.Y.). The structural formula far a typical vinyl sulfone is the following:

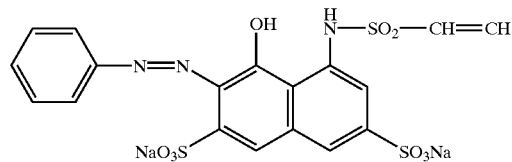

A list of vinyl sulfones includes: Remazol Red (B), Remazol Black (B), Remazol Brilliant Blue (R), Remazol Red-Violet (R), Remazol Yellow (RT) and Remazol Yellow (GN).

Urea derivatives as described in U.S. Pat. No. 3,725,525 by B. Joos, and incorporated by reference, Alkoxysilanes as described in EP0159628 by R. Stadnick and U.S. Pat. No. 4,567,039 by R. Stadnick et. al., and incorporated by reference, Isothiuroniums as described in U.S. Pat. Nos. 5,254,335 and 5,206,013 both by T. Deppert et. al., and both incorporated by reference, and Monohalotriazines and dihalotriazines, dihaloquinoxaline, dihalopyrimidines, β-haloethylsulfones, β-sulfatoethylsulfones, acrylates, methacrylates, acrylamides, methacrylamides, malemimides, halomaleimides, epoxides, aziridines and derivatives, esters, oxazolinium, imidazolium, thiazolidinium, acid derviatives of carboxylates and sulfates, esters, carbamates, anhydrides, isothiocyanates, isocyanates, lactones, and azalactones having the structure:

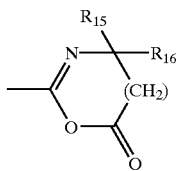

wherein Z represents the remainder of the molecule, $R_{15}$ and $R_{16}$ can be the same or different chosen from $C_1$–$C_{12}$ alkyl, $C_2$–$C_{24}$ alkenyl, $C_3$–$C_{12}$ cycloalkyl, $C_5$–$C_{26}$ aryl or $R_{15}$ and $R_{16}$ can form a carbocyclic containing 4 to 12 atoms and further wherein any $R_{15}$ and $R_{16}$ can contain 0 to 3 heteroatoms chosen from S, N, and O.

Nucleophilic reactive groups or "hooks" that may be included within reactive agents of the present inventions include, but are not limited to, the following:

thiols or thiolates as described in U.S. Pat. No. 3,484,417 by G. Kalopissis et. al., U.S. Pat. Nos. 5,935,560 and 5,935,560, both by J. Seper et. al., and U.S. Pat. No. 5,776,454 by R. Gee et. al., all incorporated by reference, thiols or thiolates containing quaternary salts as described in U.S. Pat. No. 4,973,475 by R. Schnetzinger et. al., U.S. Pat. Nos. 5,087,733 and 5,206,013 both by T. Deppert et. al., all incorporated by reference, thioalkylamides as described in U.S. Pat. No. 5,068,378 by D. Halloran et. al., incorporated by reference, thioalkyl esters as described in U.S. Pat. No. 5,350,572 by A. Savaides et. al., incorporated by reference, and cysteamine derivatives having the formula:

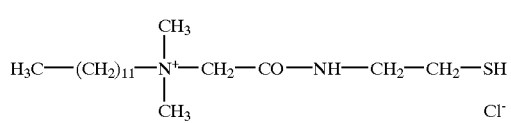

wherein the above formula is N-dodecyl-N,N-dimethyl glycine cysteamine hydrochloride, also known as N-dodecyl amino betaine mercaptoethylamine (DABM).

Protected Thiol reactive groups or "hooks" that may be included within reactive agents of the present inventions include, but are not limited to, reactive groups of the following structure:

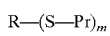

where R is a mono or multivalent cosmetically active functional group, S is sulfur, Pr is a protecting group and m is an integer between 1 and 100. The protecting group is selected from the group consisting of heterocyclic protecting groups, $sp^2$ aliphatic trigonal carbon protecting groups, $sp^3$ carbon electrophilic protecting groups, phosphorus protecting groups, metal based protecting groups, non-metal and metalloid based protecting groups, energy-sensitive protecting groups and mixtures thereof as described in U.S. patent applications having the Ser. Nos. 09/478,855 and 09/227,912, both by R. Glenn et al., and both of which are incorporated herein.

Preferred reactive groups or "hooks" of the present invention include those of the Protected Thiol type. Of the thiol protective groups, the heterocyclic protecting groups, the $sp^2$ protecting groups and the phosphorus protecting groups are preferred, with the heterocyclic protecting groups being more preferred. Of the heterocyclic protecting groups, the pyrimidinium, pyridinium, and benzothiazolium classes are preferred, with the pyrimidinium class being more preferred.

The mono or multivalent cosmetically active functional group, R, suitable for inclusion within the reactive agents of the present invention may be any moiety that imparts one or more visual, tactile or other cosmetic beneficial effects on proteinaceous materials such as keratin, hair, skin, animal fur or wool. Any cosmetic moiety may be included as a functional group in the compositions of the present invention as long as the compound can be modified to contain at least one reactive group or "hook" as described herein and in the references provided herein.

Suitable functional groups that are suitable for inclusion within the reactive agents of the present invention include, but are not limited to, antimicrobial compounds, UV-absorbing compounds, skin conditioning agents, hair conditioning agents, hair repair agents, hair styling agents, hair dyes, scalp treatment agents, anti-inflammatory compounds, antioxidants, dyes and coloring agents, perfumes, oral care actives, skin moisturizers, pharmaceutical agents, antidandruff agents, insect repellents, moisturizers, humectants, pearlescent and/or opacifying materials, fabric care actives, pet grooming actives, fabric anti-wrinkling agents, shrink-resistant actives, laundry care actives, hard surfaces actives, textile actives, textile dyes, water-proofing agents, cationic polymers, cationic surface modifiers, hydrophobic surface modifiers, anionic surface modifiers, absorbents, antifungal agents, insecticidal agents, textile color guards, nail actives such as enamel and polish, eyelash actives and mascara, antiperspirant and deodorant actives, anti-acne actives, odor control actives, fluorescent actives, bleaching agents, enzymes, antibodies, dispersing aids, emollients, stabilizers, anti-static agents, anti-seborrhea agents, optical brighteners, fluorescent dyes, softeners, cross-linking agents, photobleaches, bactericides, and mixtures thereof. Please see U.S. Ser. No. 09/478,855 by R. Glenn et. al. for a more detailed listing of cosmetic functional groups.

Preferred cosmetic functional groups include hair conditioning agents, hair repair agents, hair styling agents, and hair dyes and coloring agents. Please see U.S. Ser. No. 09/478,855 by R. Glenn et. al. for a more thorough list of preferred cosmetic functional groups.

An exemplary reactive agent to demonstrate the present invention comprises a Protected Thiol reactive group of the pyrimidinium type combined with a silicone hair conditioning cosmetic functional group. The structure of this exemplary reactive agent is as follows:

Polymer I

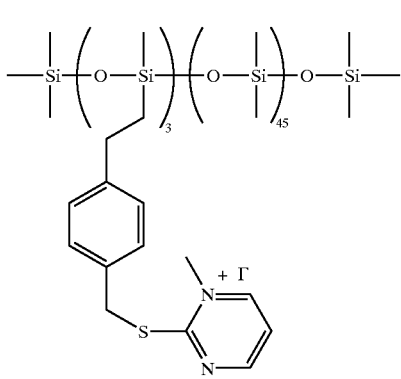

Conditioner III

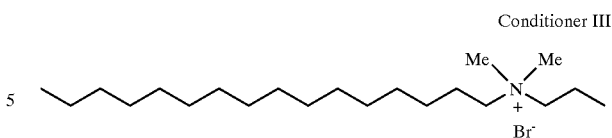

This compound and its synthesis preparation is disclosed within U.S. Ser. No. 5,087,733 by T. M. Deppert et. al. from column 6, lines 35–68 and Column 7, lines 10–15.

The reactive agent comprises from about 0.01% to 10 about 10%, more preferably from about 0.5% to about 5%, and most preferably from about 1% to about 4% by weight of the composition.

Water Immiscible Solvent

The water immiscible solvents of the present invention must be able to dissolve or disperse the reactive agent. In the case where the reactive agent is not fully soluble in the solvent, the partial solution or dispersion is such that the system is physically stable. That is, the dispersion does not settle out, or separate into more than one phase, over time. Such solutions or dispersions are often clear, but may be turbid or cloudy.

This compound and its synthesis preparation are disclosed within U.S. Ser. No. 09/478,855 by R. Glenn et. al. Polymer I is chemically shelf unstable with the pyrimidinium moiety being prone to premature hydrolysis in the presence of aqueous media.

Additional reactive agents containing a silicone hair conditioning cosmetic group are found within U.S. application Ser. No.09/616,535 by M. Butts et al., filed Jul. 14, 2000, U.S. application Ser. No. 09/616,534 by Butts et al., filed Jul. 14, 2000, U.S. application Ser. No. 09/616,533 by M. Butts et al., filed Jul. 14, 2000, and U.S. application Ser. No. 09/616,532 by M. Butts et al., filed Jul. 14, 2000, all of which are incorporated by reference herein.

The water immiscible solvents of the present compositions include, but are not limited to, the group consisting of vegetable oil, castor oil, petroleum distillates, hydrocarbon compounds, silicone compounds, esters of C6–C18 alkyl acetates, esters of C1–C4 carboxylic acid and C6–C18 al C6–C18 alkyl carbonates, C6–C18 diols, sterically hindered C6–C18 N-alkyl pyrrolidones and α-C1–C4 alkyl derivatives thereof, and mixtures thereof.

An additional exemplary reactive agent to demonstrate the present invention comprises an electrophilic reactive group of the azlactone type combined with a silicone hair conditioning cosmetic functional group. The structure of this exemplary reactive agent is as follows:

The water immiscible solvents also include, but are not limited to, a volatile or nonvolatile silicone compound, a volatile or nonvolatile hydrocarbon compound, or mixtures thereof. The volatile silicone compounds can be a linear or cyclic polydimethylsiloxane, such as hexamethylsiloxane or a cyclomethicone, available commercially under the trade names such as DOW CORNING 200 FLUID, DOW CORNING 244 FLUID, DOW CORNING 245 FLUID, DOW CORNING 344 FLUID, and DOW CORNING 345 FLUID from Dow Coming Corporation, Midland, Mich., and SILICONE SF-1173 and SILICONE SF-1202 from General Electric, Waterford, N.Y.

Polymer II

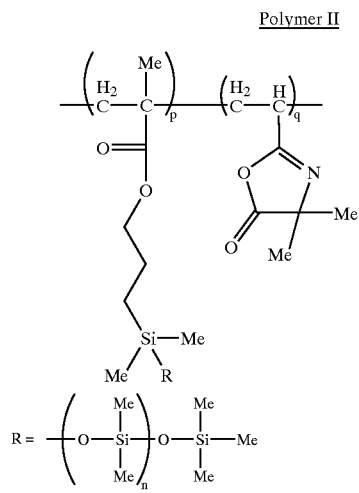

where p=1, q=14.6 and n=60. This compound and its synthesis preparation is disclosed within U.S. Ser. No. 5,525, 332 by A. D. Gough et. al. from column 12, lines 11–67 through Column 13, lines 1–18.

Volatile hydrocarbon compounds include hydrocarbons having about 10 to about 30 carbon atoms, for example, isododecane and isohexadecane, i.e., PERMETHYL 99A, PERMETHYL 101A, and PERMETHYL 102A, available from Presperse, Inc., South Plainfield, N.J. The volatile hydrocarbon compounds can also include aliphatic hydrocarbon having about 12 to about 24 carbon atoms, and having a boiling point of about 90° C. to about 250° C., i.e., ISOPAR C, ISOPAR E, ISOPAR G, and ISOPAR M, available from Exxon Chemical Co., Baytown, Tex. Other exemplary volatile hydrocarbon compounds are depicted in general structure (I):

An additional exemplary reactive agent to demonstrate the present invention comprises a cucleophilic reactive group of the thiol type combined with a hydrocarbon conditioning cosmetic functional group. The structure of this exemplary reactive agent is as follows:

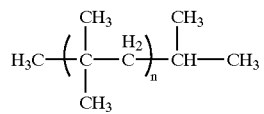

where n ranges from 2 to 5.

Additional water immiscible solvents include propylene carbonate, available commercially as ARCONATE PROPY- LENE CARBONATE, available from ARCO Chemical Company, and hydrofluoroethers, available commercially as HFE-7100, HFE-71DE, HFE-71DA, HFE-71IPA, and HFE-7200, available from 3M Chemicals.

Nonvolatile water immiscible hydrocarbon solvents include mineral oil, a pheyltrimethicone, isopropyl myristate, castor oil, or branched hydrocarbons according to structure I where n is 5–250 including PERMETHYL 104A, PERMETHYL 106A, and PERMETHYL 108A, available from Presperse, Inc., South Plainfield, N.J. Nonvolatile water immiscible solvents also include polydimethylsiloxanes having a viscosity at 25° C. of about 6 to about 400 centistokes, such as DOW CORNING 556 FLUID, or DOW CORNING 200 FLUID, respectively, available from Dow Corning Corp., Midland, Mich.

Other water immiscible solvents that can be incorporated into the compositions include, but are not limited to, branched 1-decene oligomers, like 1-decene dimer or polydecene; and esters having at least about 10 carbon atoms, and preferably about 10 to about 32 carbon atoms. Suitable esters include those comprising an aliphatic alcohol having about eight to about twenty carbon atoms, and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight-chained or branched. Preferably, the ester has a molecular weight of less than about 500. Suitable esters include, but are not limited to, a) aliphatic monohydric alcohol esters, including, but not limited to, myristyl propionate, isopropyl isostearate, isopropyl myristate, isopropyl palmitate, cetyl acetate, cetyl propionate, cetyl stearate, isodecyl neopentonoate, cetyl octanoate, isocetyl stearate; b) aliphatic di- and tri-esters of polycarboxylic acids, including, but not limited to, diisopropyl adipate, diisostearyl fumarate, dioctyl adipate, and triisostearyl citrate; c) aliphatic polyhydric alcohol esters, including, but not limited to, propylene glycol dipelargonate; d) aliphatic esters of aromatic acids, including, but not limited to $C_{12}$–$C_{15}$ alcohol esters of benzoic acid, octyl salicylate, sucrose benzoate, and dioctyl phthalate. Numerous other esters are listed in the International Cosmetic Ingredient Dictionary and Handbook, Vol. 2, Eight Ed., The Cosmetic Toiletry and Fragrance Assn., Inc., Washington, D.C. (2000) at pages 1670 through 1676, incorporated herein by reference.

The water immiscible solvent may be a di- or tri- glyceride. Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Preferred water immiscible solvents for use in the present invention include

- volatile hydrocarbon compounds having about 12 to about 24 carbon atoms, and having a boiling point of about 90° C. to about 250° C., i.e., ISOPAR C, ISOPAR E, ISOPAR G, and ISOPAR M, available from Exxon Chemical Co., Baytown, Tex.;
- volatile silicone compounds such as hexamethylsiloxane or a cyclomethicone, available commercially under the trade names such as DOW CORNING 200 FLUID, DOW CORNING 244 FLUID, DOW CORNING 245 FLUID, DOW CORNING 344 FLUID, and DOW CORNING 345 FLUID from Dow Corning Corporation, Midland, Mich., and SILICONE SF-1173 and SILICONE SF-1202 from General Electric, Waterford, N.Y; and
- propylene carbonate, available commercially as ARCONATE PROPYLENE CARBONATE, available from ARCO Chemical Company.

The water immiscible solvent comprises from about 1% to about 50%, more preferably from about 2% to about 40%, and most preferably from about 3% to about 30% by weight of the composition.

Bi-layer Structures

Amphiphilic molecules are poorly soluble in water, their critical micellar concentration is between $10^{-8}$ and $10^{-12}$ M (depending on their hydrocarbon chain length). At higher concentrations the amphiphiles form aggregates. Such aggregates vary in topology and stability depending on the structure of the amphiphilic molecule and surrounding conditions. The most common forms of amphiphile aggregates are micelles, cubic, hexagonal and lamellar phases. [See Polish Journal of Pharmacology, 1999, 51, 211–222 ISSN 1230-6002].

It is well known that in aqueous solutions, certain amphiphilic molecules and combinations form lamellar liquid crystals (neat phase) which are mesomorphic structure types between liquids, which are random, and crystals, which are periodic in three dimension. [See F. B. Rosevear, "Liquid Crystals: The Mesomorphic Phases of Surfactant Compositions", J. Soc. Cosmetic Chemists, 19, 581–594 (Aug. 19, 1968)]. Such lamellar liquid crystals consist of parallel bimolecular layers, termed bi-layers, swollen in water wherein the hydrophilic polar head groups orient toward the aqueous environment and the hydrophobic tail regions orient toward the center where they are shielded from the aqueous environments. Parallel sheets of water separate successive bi-layers to create a multi-bi-layered system.

If desired, such bi-layers can be dispersed via processing to form vesicles (also termed liposomes) wherein the bi-layers adopt a spherical configuration to surround an aqueous space. Liposomes consisting of a single bi-layer are referred to as unilamellar vesicles (ULV), and those consisting of two or more bi-layers (onion-like structures) as multilamellar vesicles (MLV). ULV's can be small (<100 nm in diameter) or large (>100 nm). MLV's can be 100 nm to >1 mm in diameter.

The bi-layers of the present invention can be in the form of flat sheets, unilamellar vesicles and multilamellar vesicles or combinations thereof.

It is preferred that the water immiscible solvent containing the reactive agent is in the form of droplets or in the form of sheets. When in the form of droplets, each droplet of the water immiscible solvent comprising the reactive agent is preferably individually surrounded by one or more bi-layers. When in the form of sheets, each sheet of the water immiscible solvent comprising the reactive agent is preferably separated from the adjacent sheet by one or more than one bi-layer. When the solvent is in the form of droplets, these preferably have a diameter of from 0.01 micrometers to 100 micrometers, more preferably from 0.1 micrometers to 50 micrometers, and most preferably from 0.5 micrometers to 10 micrometers.

Without being limited by theory, it is believed that the water immiscible solvent phase containing the reactive agent is in the form of discrete droplets enveloped in a bi-layer structure. Such bi-layer structures are then separated from each other by the aqueous continuous phase (i.e., bi-layer aqueous phase) to form a multi-bi-layered structure. The water immiscible solvent comprising the reactive agent serves as a diffusion barrier that minimizes contact between the chemically unstable reactive agent and the aqueous phase. The structured bi-layers surrounding the water immiscible solvent are a further barrier between the reactive agent and the aqueous phase and also serve to keep the reactive agent dispersed within the aqueous continuous phase over the shelf life of the composition to enable the delivery of the reactive agent to the hair in a consumer preferable medium, i.e., an aqueous emulsion cream, and without additional consumer inconvenience.

Many amphiphiles, or surfactants, are known to form bi-layers depending on the degree of packing of adjacent surfactants within aqueous solution. This degree of packing is influenced by surfactant structure as well as packing synergisms that may exist between differing surfactants within mixed surfactant systems. As a general rule of thumb, the Critical Packing Factor ($\phi$) can be utilized to visualize the surfactant structural characteristics that influence the degree of packing:

$$\phi = v/(a \times L)$$

where v is the volume occupied by hydrophobic groups within the core, a is the cross-sectional area occupied by the hydrophilic groups at the surface, and L is the length of the hydrophobic groups. For instance, as the hydrophobic group becomes bulkier, the packing will be increased. Also, it can be visualized that the addition of co-surfactants such as fatty alcohols (small a and large v and L) will also result in increased packing. While not being bound to theory, it is generally believed that the packing parameter ($\phi$) needs to be greater than 0.5 and less than or equal to 1.0 for bi-layers to be formed. If $\phi<0.5$ the formation of micelles will be favorable and if $\phi>1.0$ the formation of reverse micelles will be favorable.

Suitable surfactants for forming the bi-layer structures of this invention include cationic, anionic, nonionic, amphoteric, zwitterionic and gemini surfactants.

Examples of suitable cationic surfactants include quaternary ammonium hydroxides, e.g., tetramethylammonium hydroxide, alkyltrimethylammonium hydroxides in which the alkyl group has from about 8 to 22 carbon atoms, for example octyltrimethylammonium hydroxide, dodecyltrimethyl-ammonium hydroxide, hexadecyltrimethylammonium hydroxide, cetyltrimethylammonium hydroxide, and behenyltrimethylammonium hydroxide, benzyltrimethylammonium hydroxide, octyldimethylbenzyl-ammonium hydroxide, decetyldimethylbenzylammonium hydroxide, stearyldimethylbenzylammonium hydroxide, distearyldimethylammonium hydroxide, didodecyldimethylammonium hydroxide, dioctadecyldimethylammonium hydroxide, tallow trimethylammonium hydroxide, cocotrimethyl-ammonium hydroxide, and their corresponding salts, e.g., halide. Cetylpyridinium hydroxide and its corresponding salts, e.g. halide. Preferred cationic surfactants are cetyltrimethylammonium chloride (CTAC) and cetyltrimethylammonium bromide (CTAB). CTAB 99% from Fluka, CTAC 50% (Arquad 16-50, Akzo). Preferably, cationic surfactants are used at 2–10% with CTAC and CTAB being the preferred cationic surfactants. Additionally, when cationic surfactants are used, it is preferred to also employ cholesterol wherein the ratio of cholesterol to cationic surfactant ranges from 0.1:1.0 to 1.0:1.0, more preferably from 0.5:1.0 to 1.5:1.0, and most preferably 0.7:1.0 to 1.25:1.0.

Non-ionic surfactants suitable for use in the compositions of the present invention include condensation products of aliphatic (C8 to C18) primary or secondary linear or branched chain alcohols or phenols with alkylene oxides, usually ethylene oxide, and generally having from 6 to 30 ethylene oxide groups.

Other suitable non-ionic surfactants include mono- or di-alkyl alkanolamides. Examples include coco mono- or di-ethanolamide or coco-isopropanolamide. Further suitable nonionic surfactants are the alkyl polyglycosides (APG's). Typically, the APG is one which comprises an alkyl group connected (optionally via a bridging group) to a block of one or more glycosyl groups. Preferred APG's are described by the following formula:

wherein R is a branched or straight chain alkyl group which may be saturated or unsaturated, and G is a saccharide group. R may represent a mean alkyl chain length from about $C_5$ to about $C_{20}$. Preferably, R represents a mean alkyl chain length of from about $C_8$ to about $C_{12}$. G may be selected from $C_5$ or $C_6$ monosaccharide residues, or mixtures of $C_5$ and $C_6$ monosaccharide residues, and is preferably a glucoside. G may be selected from the group comprising glucose, xylose, fructose, mannose and derivatives thereof. Preferably, G is glucose. The degree of polymerization, n, may have a value of from about 1 to about 10 or more. Preferably, the value of n lies in the range of from about 1.1 to about 2. Most preferably, the value of n lies in the range of from about 1.3 to about 1.5. Suitable alkyl polyglucosides for use in the present invention are commercially available and include, for example, those materials identified as Oramix NS10 from Seppic Inc., APG225, APG230, APG350, APG550 and APG600 from Henkel Corporation.

Esters of polyols and sugars, the polyethoxylated and/or polypropoxylated alkylphenols, the polyhydroxylated polyethers of fatty alcohols, fatty acid alkanolamides, amine oxides, and the condensation products of ethylene oxide with long chain amides are also representative of suitable nonionic surfactants.

Preferred nonionic surfactants include cetearyl alcohol, cetearyl glucoside, cetostearyl alcohol and ceteareth 20.

Amphoteric and zwitterionic surfactants suitable for use in compositions of the invention may include alkyl amine oxides, alkyl betaines, alkyl amidopropyl betaines, alkyl sulfobetaines, alkyl glycinates, alkyl carboxyglycinates, alkyl amphopropionates, alkulamphoglycinates, alkyl amidopropyl hydroxy-sultaines, acyl taurates and acyl glutamates, wherein the alkyl and acyl groups have from abut 8 to 19 carbon atoms. Examples include lauryl amine oxide, cocodimethyl sulphopropyl betaine and preferably lauryl betaine, cocamidopropyl betaine and sodium cocamphoproprionate.

Suitable anionic surfactants are the alkyl sulfonates, alkyl ether sulfonates, alkylaryl sulfonates, alkanoyl isethionates, alkyl succinates, alkyl sulfosuccinates, N-alkoyl sarcosinates, alkyl phosphates, alkyl ether phosphates, alkyl ether carboxylates, and alpha-olefin sulfonates, especially their sodium, magnesium, ammonium and mono-, di- and triethanolamine salts. The alkyl and acyl groups generally contain from 8 to 18 carbon atoms and may be unsaturated. The alkyl ether sulfates, alkyl ether phosphates and alkyl ether carboxylates may contain from one to 10 ethylene oxide or propylene oxide units per molecule. A preferred anionic surfactant includes cetearyl phosphate.

Gemini surfactants are made up of two long hydrocarbon chains ($C_{12}$–$C_{22}$) and two ionic head groups linked by a short spacer. The spacer is attached directly to the identical ionic groups, each of which is in turn bonded to an identical hydrocarbon chain. The spacer can vary in length, hydrophobicity and flexibility and is typical a $C_2$–$C_5$ divalent alkyl radical. A typical gemini surfactant is as follows:

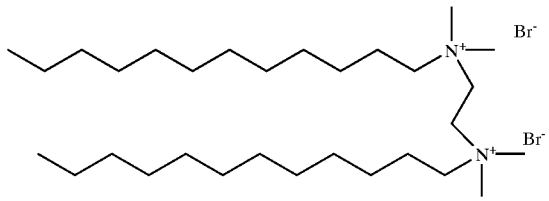

Gemini surfactants are described further in the book: Surfactants and Polymers in Aqueous Solution, by Bo Jonsson, Bjorn Lindman, Krister Holmberg and Bengt Kronberg, pages 4–5, John Wiley and Sons, ©1998.

Optional surfactants which may be included are fatty alcohols or fatty acids, or derivatives thereof, or a mixture of any of these, having a chain length of from about 8 to about 28 carbon atoms, preferably from about 12 to 18 carbon atoms. These materials may be predominantly linear or may be branched. Such fatty material(s) may be present in a total amount of from about 0.001 to 20% by weight, more preferably 0.01 to 10%, even more preferably 0.1 to 1%.

The bi-layers may also be formed from lipid surfactants including either phospholipids, i.e., based on glycerol and sphingosine, or glycolipid, i.e. based on sphingosine. Phospholipids are preferred with phosphatidyl choline (lecithin) being the preferred phospholipid. Of the alcohol moieties which comprise the phosphoglycerides, serine, choline and ethanolamine are particularly preferred, and of the fatty chains, those having a chain length of C14 to C24 are preferred. The fatty acid chains may be branched or unbranched, saturated or unsaturated, and palmitic, myristic, oleic, stearic, arachidonic, linolenic, linoleic and arachidic acids are particularly preferred.

The surfactant(s) may be present in the composition in a total amount of from about 1 to 50% by weight, preferably from 2 to 40% by weight, more preferably from 5 to 30% by weight.

In cases wherein the reactive agent is charged, i.e., cationic or anionic, it is preferable that the surfactant bi-layers are comprised of surfactants with the same net charge as the reactive agent to confer additional chemical shelf stability, e.g., cationic bi-layers for cationic reactive agents and anionic bi-layers for anionic reactive agents.

The bi-layers may be comprised of one or more differing surfactants or lipid surfactants of the same or differing classes. The bi-layers may be in the form of closed vesicles that may be unilamellar or multilamellar or in the form of flat sheets or combinations thereof. When spherical vesicles are formed, their size can be from 0.1 to 10 microns.

The presence of liquid crystalline bi-layers, neat phase, can be detected with the use of a polarizing microscope as is taught in "The Microscopy of the Liquid Crystalline Neat and Middle Phases of Soaps and Synthetic Detergents", by F. B. Rosevear in The Journal of the American Oil Chemists' Society, Vol. 31, (December 1954).

Numerous techniques can be employed to produce the bi-layers as flat sheets or vesicles as desired. In general these techniques involve mixing the components that form the bi-layer, as well as any components that are to be incorporated within the bi-layers, under conditions that permit the formation of the bi-layers.

The specific method for producing the bi-layers and incorporating the water immiscible solvent comprising the reactive component is not critical. Generally, the bi-layers are formed by simple mixing or high shear mixing with the addition of the water immiscible solvent comprising the reactive component either at the beginning, middle or end of the process.

The bi-layers may also be prepared by conventional techniques that are employed in the formation of vesicles, i.e. liposomes. For example by exposure of aqueous solutions or suspensions of surfactants to ultrasonic energy. The bi-layers may also be prepared in known manner by injection of a solution of the surfactants in a water-soluble or water-miscible organic solvent, e.g., ethanol, through a narrow orifice into an aqueous medium. Alternatively, the bi-layers may be formed by contacting a solution of the surfactants in an organic oil with water, with the input of sufficient mechanical energy, preferably ultrasonic energy, whereupon the surfactants leach into the water and vesicles form at the interface. Furthermore, the bi-layers may be formed via a microfluidizer as described in Mayhew et. al. "Characterization of Liposomes Prepared Using a Microemulsifier," Biochem. et Biophys. Acta., 775, 169-74 (1984).

Aqueous Continuous Phase

The treatment compositions of the present invention include an aqueous continuous phase. The aqueous continuous phase comprises water and optional components that are fully soluble within the aqueous continuous phase. In one embodiment, the aqueous phase may comprise conventional hair treatment chemicals including:

hair bleaching agents including, but not limited to, hydrogen peroxide, sodium percarbonate, sodium perborate, magnesium perborate, magnesium dioxide, barium binoxide and combinations thereof;

hair permanent wave agents including, but not limited to, thioglycolic acid, thiolactic acid, cysteine, thioglycerol, thioglycollic hydrazide, thioglycolamide, and glycerol monothioglycollate, salts of hydrogen sulfide, salts of hydrogen cyanide, trihydroxymethyl phosphine or its precursor, tetrahydroxymethyl phosphonium chloride, borohydride, dithionite, hydrosulfite, and sulfoxylate and combinations thereof;

oxidative hair dyes including, but not limited to, p-phenylenediamine, toluene-2,5-diamine, 2-methoxy-p-phenylenediamine, 2-chloro-p-phenylenediamine, toluene-3,4-diamine,o-amino-phenol, p-aminophenol, resorcinol, 1-naphthol, pyrogallol, 4-chlororesorcinol, 4-methoxy-m-phenylenediamine, m-phenylenediamine, hydroquinone and mixtures thereof.

semi-permanent hair dyes including, but not limited to, 2-nitro-p-phenylenediamine, 4-nitro-o-phenylenediamine, HC red No. 3, HC yellow No. 2, HC yellow No. 4, HC blue No. 1, HC red No. 1, HC orange No. 1, Disperse black 9, Acid orange 3, Disperse violet 1, Disperse blue 1 and mixtures thereof.

hair swelling agents including, but not limited to, urea, thiourea, acetic acid, phosphoric acid, formic acid, formamide, ethyl amine, alkali halides such as potassium iodide, sodium bromide, lithium bromide, and lithium chloride, and mixtures thereof.

The composition contains from about 20% to about 95%, by weight of the composition, of an aqueous continuous phase.

Optional Components

The topical composition according to the invention may include optional benefit materials and cosmetic adjuncts, as long as the benefit materials or the adjuncts do not eliminate or substantially reduce the performance or chemical shelf stability of the reactive agent. The additional ingredients may include, for example dyes and coloring agents, fragrances; anionic, cationic, non-ionic, amphoteric or zwitterionic surfactants; buffers, masking fragrances, dispersing agents, stabilizers, cationic polymers, perfumes, non-ionic polymers, anionic polymers, complex coacervates, complex coacervate capsules, metal salts, lewis acids, buffering agents, particulate thickeners, polymeric thickeners, wax thickeners, oils, emollients, humectants, moisturizers, dyes, dyes and coloring agents, pearlescents, opacifiers, enzymes, suspending agents, antimicrobials, preservatives, proteins, herb and plant extracts, bleach, peroxide, polyols, silicones, oils, antibodies, pH adjusting agents including pH buffers, viscosity modifiers, preservatives, viscosity enhancers, gelling agents, chelators, silicones, emulsifying agents, moisturizing and conditioning agents, and other common adjuvants well known to those skilled in the art.

An antioxidant may also be incorporated within the composition. Suitable antioxidants include vitamin E and its derivatives, BHT and BHA.

The composition of the present invention may optionally contain from about 0.1% to about 10%, preferably from about 0.25% to about 8%, more preferably from about 0.5% to about 5% of a stabilizer. The stabilizer is used to form a stabilizing network within the bi-layer emulsion that prevents phase separation.

In one embodiment of the present invention, the stabilizer can comprise a crystalline, hydroxyl-containing stabilizer. The crystalline, hydroxy-containing stabilizer is selected from the group consisting of:

(i)

$$H_2C-O-R_1$$
$$HC-O-R_2$$
$$H_2C-O-R_3$$

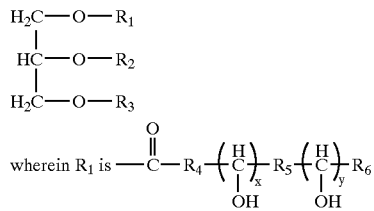

wherein $R_1$ is $-\overset{O}{\overset{\|}{C}}-R_4-\left(\overset{H}{\underset{|}{\overset{|}{C}}}\right)_x-R_5-\left(\overset{H}{\underset{|}{\overset{|}{C}}}\right)_y-R_6$ $R_2$ is $R_1$ or H
$R_3$ is $R_1$ or H
$R_4$ is $C_{0-20}$ Alkyl
$R_5$ is $C_{0-20}$ Alkyl
$R_6$ is $C_{0-20}$ Alkyl
$R_4+R_5+R_6=C_{0-22}$
and wherein $1 \leq x+y \leq 4$;

(ii)

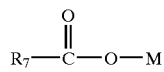

$$R_7-\overset{O}{\overset{\|}{C}}-O-M$$

wherein $R_7$ is $-R_4(CHOH)_xR_5(CHOH)_yR_6$
M is $Na^+$, $K^+$ or $Mg_{++}$, or H; and
iii) mixtures thereof;

Some preferred hydroxyl-containing stabilizers include 12-hydroxystearic acid, 9,10-dihydroxystearic acid, tri-9,10-dihydroxystearin and tri-12-hydroxystearin (hydrogenated castor oil is mostly tri-12-hydroxystearin). Tri-12-hydroxystearin is most preferred for use in the emulsion compositions herein.

When these crystalline, hydroxyl-containing stabilizers are utilized in the personal cleansing compositions herein, they are typically present at from about 0.5% to 10%, preferably from 0.75% to 8%, more preferably from 1.25% to about 5% of the treatment compositions. The stabilizer is insoluble in water under ambient to near ambient conditions.

Alternatively, the stabilizer employed can comprise a polymeric thickener. When polymeric thickeners as the stabilizer in the personal cleansing compositions herein, they are typically included in an amount ranging from about 0.01% to about 5%, preferably from about 0.3% to about 3%, by weight of the composition. The polymeric thickener is preferably an anionic, nonionic, cationic or hydrophobically modifier polymer selected from the group consisting of cationic polysaccharides of the cationic guar gum class with molecular weights of 1,000 to 3,000,000, anionic cationic and nonionichomopolymers derived from acrylic and/or methacrylic acid, anionic cationic and nonionic cellulose resins, cationic copolymers of dimethyldialkylammonium chloride and acrylic acid, cationic homopolymers of dimethylalkyl-ammonium chloride, cationic polyalkylene and ethoxypolyalkylene imines, polyethylene glycol of molecular weight from 100,000 to 4,000,000, and mixtures thereof. Preferably, the polymer is selected from the group consisting of Sodium Polyacrylate, hydroxy ethyl Cellulose, Cetyl Hydroxy Ethyl Cellulose, and Polyquaternium 10.

The polymeric thickener is preferably and anionic, nonionic, cationic or hydrophobically modified polymer of natural, modified natural or synthetic origin from plants, microbials, animals or petroleum raw materials including karaya gum, tragacanth gum, gum arabic, gum ghatti, guar gum, locust bean gum, quince seed, psyllium seed, tamarind seed, carrageenan, alginates, agar, larch gum, pectins, starches, xanthan gum, dextran, casein, gelatin, keratin, shellac, cellulose derivatives, guar derivatives, acrylic acid polymers, polyacrylamides, and alkylene/alkylene oxide polymers. Preferred polymeric thickeners include guar gum, available commercially as SUPERCOL U, U NF, SUPERCOL GF, SUPERCOL G2S, and SUPERCOL G3 NF from Aqualon and JAGUAR GUM from Rhone-Poulenc; xanthan gum, available commercially as KELTROL CG, KELTROL CG F, KELTROL CG T, KELTROL CG TF, KELTROL CG 1000, KELTROL CG RD, KELTROL CG GM, KELTROL CG SF, from Calgon, and RHODICARE S, RHODICARE XC, RHODICARE H, AND RHODICARE D, from Rhone-Poulenc; hydroxyethylcellulose, available commercially as NATRASOL 210 types and NATRASOL 250 types from Aqualon; hydroxypropyl guar, available commercially as JAGUAR HP-8, JAGUAR HP-11, JAGUAR HP-60, and JAGUAR H-79 from Rhone-Poulenc. Additional specific polymeric thickeners that are suitable for the present invention are given in *Rheological Properties of Cosmetics and Toiletries*, edited by Dennis Laba, 1993, by Marcel Dekker, Inc. on pages 57 through 121 (ISBN 0-8247-9090-1).

Alternatively, the stabilizer employed can comprise C10–C22 ethylene glycol fatty acid esters. C10–C22 ethylene glycol fatty acid esters can also desirably be employed in combination with the polymeric thickeners hereinbefore described. The ester is preferably a diester, more preferably a C14–C18 diester, most preferably ethylene glycol distearate. When C10–C22 ethylene glycol fatty acid esters are utilized as the stabilizer in the personal cleansing compositions herein, they are typically present at from about 3% to about 10%, preferably from about 5% to about 8%, more preferably from about 6% to about 8% of the treatment compositions.

Another class of stabilizer which can be employed is dispersed amorphous silica. As used herein the term "dispersed amorphous silica" refers to small, finely divided non-crystalline silica having a mean agglomerate particle size of less than about 100 microns. Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates, precipitated silicas and silica gels are generally made in aqueous solution. See, Cabot Technical Data Pamphlet TD-100 entitled "CAB-O-SIL.RTM. Untreated Fumed Silica Properties and Functions", October 1993, and Cabot Technical Dat Pamphlet TD-104 entitled "CAB-O-SIL.RTM. Fumed Silica in Cosmetic and Personal Care Products", March 1992, both of which are herein incorporated by reference.

The fumed silica preferably has a mean agglomerate particle size ranging from about 0.1 microns to about 100 microns, preferably from about 1 micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from about 0.2 microns to about 0.3 microns. The silica preferably has a surface area greater than 50 sq. m/gram, more preferably greater than about 130 sq. m./gram, most preferably greater than about 180 sq. m./gram.

When amorphous silicas are used as the stabilizer herein, they are typically included in the compositions at levels ranging from about 0.1% to about 10%, preferably from about 0.25% to about 8%, more preferably from about 0.5% to about 5%.

A fourth class of stabilizer which can be employed comprises dispersed smectite clay selected from the group consisting of bentonite and hectorite and mixtures thereof. Bentonite is a colloidal aluminum clay sulfate. See Merck Index, Eleventh Edition, 1989, entry 1062, p. 164, which is incorporated by reference. Hectorite is a clay containing sodium, magnesium, lithium, silicon, oxygen, hydrogen and fluorine. See Merck Index, eleventh Edition, 1989, entry 4538, p. 729, which is herein incorporated by reference. When smectite clay is employed as the stabilizer in the treatment compositions of the present invention, it is typically included in amounts ranging from about 0.1% to about 10%, preferably from about 0.25% to about 8%, more preferably from about 0.5% to about 5%.

Aqueous organic solvents may also be included, provided that they do not destabilize the bi-layers.

For use, the composition may be provided at a pH from about 3 to 11, preferably from 4 to 10.

Product Form

The treatment compositions according to the invention may be provided in any suitable physical form, for example as low to moderate viscosity liquids, lotions, milks, mousses, dispersions, sprays, gels, foams, aerosols, and creams. These compositions may be produced by procedures well known to the skilled artisan. The cosmetic compositions can be used in various manners as other known compositions in the art including but not limited to various rinse-off and leave-on applications such as hair shampoos, skin cleansers, skin lotions, hair conditioners, hair dyes, hair permanent waves, hair straighteners, hair bleaches, styling sprays, hair mousses, two-in-one shampoos, fabric softeners, lotions, nail polishes, hair serums, hair dyes, hair waving, etc.

The cosmetic composition of the present invention can be formulated as a fluid, lotion, fluid cream or cream having a viscosity from 500 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for hand or finger operation. When the composition is a cream, it can simply be stored in a non-deformable bottle or squeeze container, such as a tube or a lidded jar.

Method of Use

The compositions of the present invention can be applied to wet hair, partially wet hair or dry hair. The composition is applied to the hair with the hands, which may be gloved, and massaged in thoroughly. If desired, the composition can be mixed with additional water or separate composition prior to or during application to the hair. The contact time between the cosmetic composition of the present invention and the substrate can vary between 10 seconds and about 1 hour, preferably between 20 seconds and 30 minutes, more preferably between 30 seconds and 15 minutes. The composition is then thoroughly rinsed from the hair, though the composition can be applied as a leave-on product.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

All percentages herein are based upon the total weight of the compositions, and all such weight percentages as they pertain to listed ingredients are based on the active level and, therefore, do not include carriers or by-products that may be included in commercially available materials.

Example I

A Non-limiting Example of a Conditioning Treatment Composition

| Ingredient | w/w total composition |
| --- | --- |
| Polymer 1[1] | 2.00% |
| Isopar C[2] | 9.75% |
| Jaguar HP105[3] | 0.75% |
| Cetyltrimethylammonium chloride[4] | 7.00% |
| Cholesterol[5] | 7.00% |
| Deionized water | q.s. |

[1]Polymer 1 is as described herein, the preparation of which can be referenced in U.S. Ser. No. 09/478,855 by R. Glenn et. al.
[2]Available from Exxon
[3]Available from Rhone-Poulenc
[4]25 wt % in solution, obtained from Aldrich, item #C29, 273–7
[5]95%, obtained from Aldrich, item #C7520–9

Jaguar HP 105 is added to the water which is heated to 60 C. to solubilize the thickener. The heat is turned off. Cetyltrimethylammonium chloride is added along with the cholesterol while stirring under high shear using an IKA Ultra Turrax mixer. Polymer 1 is dissolved within the Isopar C under stirring for several hours to fully dissolve the polymer. The resulting pre-mix is then added to the cooled surfactant mixture and high sheared for several minutes.

Example II

A Non-limiting Example of a Conditioning Treatment Composition

| Ingredient | w/w total composition |
| --- | --- |
| Polymer 1[1] | 2.00% |
| Isopar C[2] | 9.75% |
| Hydroxyethylcellulose[3] | 0.50% |
| Cetyltrimethylammonium chloride[4] | 10.00% |
| Cholesterol[5] | 10.00% |
| Deionized water | q.s. |

[1]Polymer 1 is as described herein, the preparation of which can be referenced in U.S. Ser. No. 09/478,855 by R. Glenn et. al.
[2]Available from Exxon
[3]Available as Natrasol 250 from Aqualon
[4]25 wt % in solution, obtained from Aldrich, item #C29, 273–7
[5]95%, obtained from Aldrich, item #C7520–9

Hydroxyethylcellulose is added to the water which is heated to 60° C. to solubilize the thickener. The heat is turned off. Cetyltrimethylammonium chloride is added along with the cholesterol while stirring under high shear using an IKA Ultra Turrax mixer. Polymer 1 is dissolved within the Isopar C under stirring for several hours to fully dissolve the polymer. The resulting polymer pre-mix is then added to the cooled surfactant mixture and high sheared for several minutes.

Example III

A Non-limiting Example of a Conditioning Treatment Composition

| Ingredient | w/w total composition |
| --- | --- |
| Polymer 1[1] | 2.00% |
| Isopar C[2] | 9.75% |
| Xanthan Gum[3] | 0.60% |
| Arlatone 2121[4] | 7.50% |
| Deionized water | q.s. |

[1]Polymer 1 is as described herein, the preparation of which can be referenced in U.S. Ser. No. 09/478,855 by R. Glenn et. al.
[2]Available from Exxon
[3]Available from Aldrich, item #28, 602–8
[4]Available from Unichem (formerly ICI surfactants)
[5]95%, obtained from Aldrich, item #C7520–9

Xanthan gum is added to the water which is heated to 60° C. to solubilize the thickener. The heat is turned off. Arlatone 2121 is added while stirring under high shear using an IKA Ultra Turrax mixer. Polymer 1 is dissolved within the Isopar C under stirring for several hours to fully dissolve the polymer. The resulting polymer pre-mix is then added to the cooled surfactant mixture and high sheared for several minutes.

Example IV

A Non-limiting Example of a Conditioning Treatment Composition

| Ingredient | w/w total composition |
| --- | --- |
| Polymer 1[1] | 2.00% |
| Isopar C[2] | 9.75% |
| Didodecyldimethylammonium bromide (DDAB)[3] | 1.00% |
| 3-sn-Phasphatidylcholine from Soybean[4] | 10.00% |
| Cholesterol[5] | 9.60% |
| Deionized water | q.s. |

[1]Polymer 1 is as described herein, the preparation of which can be referenced in U.S. Ser. No. 09/478,855 by R. Glenn et. al.
[2]Available from Exxon
[3]98%, obtained from Aldrich, item #35, 902–5
[4]Available from Fluka, item #61758
[5]95%, obtained from Aldrich, item #C7520–9

Cholesterol, 3-sn-Phosphatidylcholine from Soybean and DDAB are added to DI water which is heated to 60° C. The heat is turned off. The mixture is stirred under high shear using an IKA Ultra Turrax mixer. Polymer 1 is dissolved within the Isopar C under stirring for several hours to fully dissolve the polymer. The resulting polymer pre-mix is then added to the cooled surfactant mixture and high sheared for several minutes.

Example V

A Non-limiting Example of a Conditioning Treatment Composition

| Ingredient | w/w total composition |
| --- | --- |
| Polymer 1[1] | 2.00% |
| Propylene Carbonate[2] | 9.75% |
| Hydroxyethylcellulose[3] | 0.50% |
| Cetyltrimethylammonium chloride[4] | 10.00% |
| Cholesterol[5] | 10.00% |
| Deionized water | q.s. |

[1]Polymer 1 is as described herein, the preparation of which can be referenced in U.S. Ser. No. 09/478,855 by R. Glenn et. al.
[2]Available from Huntsman
[3]Available as Natrasol 250 from Aqualon
[4]25 wt % in solution, obtained from Aldrich, item #C29, 273–7
[5]95%, obtained from Aldrich, item #7520–9

Hydroxyethylcellulose is added to the water which is heated to 60° C. to solubilize the thickener. The heat is turned off. Cetyltrimethylammonium chloride is added along with the cholesterol while stirring under high shear using an IKA Ultra Turrax mixer. Polymer 1 is dissolved within the Propylene carbonate under stirring for several hours to fully dissolve the polymer. The resulting polymer pre-mix is then added to the cooled surfactant mixture and high sheared for several minutes.

Example VI

A Non-limiting Example of a Conditioning Peroxide Treatment Composition for Use in Either an Oxidative Hair Colorant or Hair Bleach

| Ingredient | w/w total composition |
| --- | --- |
| Polymer 1[1] | 2.00% |
| Isopar C[2] | 9.75% |
| Hydroxyethylcellulose[3] | 0.50% |
| Cetyltrimethylammonium chloride[4] | 10.00% |
| Cholesterol[5] | 10.00% |
| Hydrogen peroxide[6] | 9.00% |
| Citric Acid[7] | to pH 4 |
| Phosphoric Acid[8] | 1.00 |
| Deionized water | q.s. |

[1]Polymer 1 is as described herein, the preparation of which can be referenced in U.S. Ser. No. 09/478,855 by R. Glenn et. al.
[2]Available from Exxon
[3]Available as Natrasol 250 from Aqualon
[4]25 wt % in solution, obtained from Aldrich, item #C29, 273–7
[5]95%, obtained from Aldrich, item #C7520–9
[6]27.5%, obtained from Aldrich, item #C43, 327–6
[7]99.5%, obtained from Aldrich, item #C25, 127–5
[8]85%, obtained from Aldrich, item #C21, 510–4

Hydroxyethylcellulose is added to the water which is heated to 60° C. to solubilize the thickener. The heat is turned off. Cetyltrimethylammonium chloride is added along with the cholesterol while stirring under high shear using an IKA Ultra Turrax mixer. The mixture is cooled and the phosphoric acid and the hydrogen peroxide is added. Citric acid is added dropwise to adjust pH to approximately 4.0. Polymer 1 is dissolved within the Isopar C under stirring for several hours to fully dissolve the polymer. The resulting polymer pre-mix is then added to the cooled surfactant mixture and high sheared for several minutes.

For hair bleaching, the above peroxide treatment composition is mixed with a separate Hair Lightener Base composition (alkalinity) and optionally a Booster Powder composition (accelerator) just prior to application to the hair. Approximately 50–100 grams of the peroxide treatment composition is added to approximately 50–100 grams of the Lightener Base composition and then approximately 10 to 40 grams of the booster powder is added. For exemplary compositions of the Hair Lightener Base and the Booster Powder composition, please reference *The Chemical and Physical Behavior of Human Hair, Third Edition*, by Clarence Robbins, 1994 by Springer-Verlag New York, Inc. pages 131–133.

For oxidative hair coloring, the above peroxide treatment composition is mixed with a separate Precursor-coupler base composition (comprises dye precursors, dye couplers and alkalinity) just prior to application to the hair. Approximately 50–100 grams of the peroxide treatment composition is added to approximately 50–100 grams of the Precursor-coupler base composition and mixed prior to application. For exemplary compositions of the Precursor-coupler base composition, please reference *The Chemical and Physical Behavior of Human Hair, Third Edition*, by Clarence Robbins, 1994 by Springer-Verlag New York, Inc. pages 247–249.

Example VII

A Non-limiting Example of a Conditioning Treatment Composition

| Ingredient | w/w total composition |
| --- | --- |
| Polymer 1I[1] | 2.00% |
| Isopar C[2] | 9.75% |
| Jaguar HP1053 | 0.75% |
| Cetyltrimethylammonium chloride[4] | 7.00% |
| Cholesterol[5] | 7.00% |
| Deionized water | q.s. |

[1]Polymer 2 is as described herein, the preparation of which can be referenced in U.S. Ser. No. 5,525,332 by A. D. Gough et. al.
[2]Available from Exxon
3 Available from Rhone-Poulenc
[4]25 wt % in solution, obtained from Aldrich, item #C29, 273–7
[5]95%, obtained from Aldrich, item #C7520–9

Jaguar HP105 is added to the water which is heated to 60 C. to solubilize the thickener. The heat is turned off. Cetyltrimethylammonium chloride is added along with the cholesterol while stirring under high shear using an IKA Ultra Turrax mixer. Polymer II is dissolved within the Isopar C under stirring for several hours to fully dissolve the polymer. The resulting pre-mix is then added to the cooled surfactant mixture and high sheared for several minutes.

Example VIII

A Non-limiting Example of a Conditioning Treatment Composition

| Ingredient | w/w total composition |
| --- | --- |
| Conditioner 3[1] | 2.00% |
| Isopar C[2] | 9.75% |
| Hydroxyethylcellulose[3] | 0.50% |

-continued

| Ingredient | w/w total composition |
| --- | --- |
| Cetyltrimethylammonium chloride[4] | 10.00% |
| Cholesterol[5] | 10.00% |
| Deionized water | q.s. |

[1]Conditioner 3 is as described herein, the preparation of which can be referenced in U.S. Ser. No. 5,087,733 by T. M. Deppert et. al.
[2]Available from Exxon
[3]Available as Natrasol 250 from Aqualon
[4]25 wt % in solution, obtained from Aldrich, item #C29, 273–7
[5]95%, obtained from Aldrich, item #C7520–9

Hydroxyethylcellulose is added to the water which is heated to 60° C. to solubilize the thickener. The heat is turned off. Cetyltrimethylammonium chloride is added along with the cholesterol while stirring under high shear using an IKA Ultra Turrax mixer. Conditioner 3 is dissolved within the Isopar C under stirring for several hours to fully dissolve the polymer. The resulting polymer pre-mix is then added to the cooled surfactant mixture and high sheared for several minutes.

What is claimed is:

1. A treatment composition, comprising:
   i) an aqueous continuous phase;
   ii) a reactive component comprising a reactive agent comprising a compound comprising a reactive group, the reactive group being a protected thiol reactive group having the formula

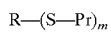

$R-(S-Pr)_m$ where R is a mono or multivalent cosmetically active functional group, wherein R is a functional group selected from the group consisting of, skin conditioning agents, hair conditioning agents, hair repair agents, hair styling agents, hair dyes, scalp treatment agents, anti-inflammatory compounds, antioxidants, perfumes, oral care actives, skin moisturizers, pharmaceutical agents, antidandruff agents, moisturizers, humectants, pearlescent and/or opacifying materials, nail actives such as enamel and polish, eyelash actives and mascara, antiperspirant and deodorant actives, anti-acne actives, odor control actives, fluorescent actives, bleaching agents, enzymes, antibodies, dispersing aids, emollients, stabilizers, anti-static agents, anti-seborrhea agents, and mixtures thereof, S is sulfur, Pr is a protecting group, wherein the protecting group is selected from the group consisting of heterocyclic protecting groups, $sp^2$ aliphatic trigonal carbon protecting groups, $sp^3$ carbon electrophilic protecting groups, phosphorus protecting groups, metal based protecting groups, nonmetal and metalloid based protecting groups other than phosphorus, energy-sensitive protecting groups and mixtures thereof, and m is an integer between 1 and 100; and b) a water immiscible solvent, wherein the water immiscible solvent solubilizes the reactive agent; and
   iii) a cationic surfactant comprising a quaternary ammonium halide wherein the cationic surfactants emulsify the reactive component in the aqueous phase to form bi-layer emulsion
   wherein the composition further comprises cholesterol wherein the ratio of cholesterol to cationic surfactant ranges from about 0.5:1.0 to about 1.5:1.0.

2. A treatment composition according to claim 1, wherein the reactive agent is covalently reactive with an amino acid based substrate.

3. A treatment composition according to claim 2, wherein the reactive agent is covalently reactive with human hair.

4. A treatment composition according to claim 1, wherein the treatment composition comprises from about 0.01% to about 10% by weight of the composition, of the reactive agent from about 1% to about 50% by weight of the composition of the water immiscible solvent; from about 1% to about 50%, by weight of the composition, of the cationic surfactants; and from about 20% to about 95%, by weight of the composition, of the aqueous continuous phase.

5. A treatment composition according to claim 1, wherein the water immiscible solvent comprises solvents selected from the group consisting of a volatile silicone compounds, nonvolatile silicone compounds, volatile hydrocarbons, nonvolatile hydrocarbons, propylene carbonates and mixtures thereof.

6. A treatment composition according to claim 5, wherein the water immiscible solvent comprises solvents selected from the group consisting of linear and cyclic polydimethylsiloxanes and mixtures thereof.

7. A treatment composition according to claim 6, wherein the water immiscible solvent comprises hexamethyl siloxane and cyclomethicone.

8. A treatment composition according to claim 7, wherein the water immiscible solvent is selected from volatile and nonvolatile hydrocarbon compounds having about 10 to 30 carbon atoms.

9. A treatment composition according to claim 8, wherein the water immiscible solvent comprises compound depicted by the following general structure wherein n ranges from 2 to 5,

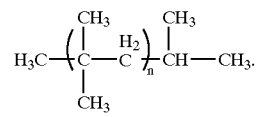

10. A treatment composition according to claim 1, wherein the treament composition further comprises a surfactant chosen from the group consisting of anionic surfactants, nonionic surfactants, amphoteric surfactants, zwitterionic surfactants, and mixtures thereof.

11. A treatment composition according to claim 10, wherein the treatment composition further comprises a liquid surfactant wherein the liquid surfactant is a phospholipid from about 1% to about 20%.

12. A treatment composition according to claim 10, wherein the treatment composition further comprises from about 1% to about 20% of a nonionic surfactant.

13. A treatment composition according to claim 1, wherein the reactive agent is charged.

14. A treatment composition according to claim 1, wherein the reactive agent is charged and the surfactants have the same net charge as the reactive agent.

15. A treatment composition according to claim 1, wherein the treatment composition comprises from about 1% to about 4%, by weight, of thiol pyrimidinium, from about 3% to about 30%, by weight, of a volatile hydrocarbon compound having about 12 to about 24 carbon atoms and having a boiling point of about 90° C. to about 250° C. from about 5% to about 30%, by weight, of cetyltrimethylammonium chloride, from about 7% to about 20% cholesterol, and from about 36% to about 91%, by weight, of the aqueous continuous phase.

16. A treatment composition according to claim 15, wherein the treatment composition further comprises from about 0.1% to about 10%, by weight, of a crystalline, hydroxyl-containing stabilizer.

17. A method of treating amino acid based substrates, wherein the amino based substrates comprises protelnaceous materials found in hair, skin, nails and wool, by applying to the substrates an effective amount of composition according to claim 1, wherein the composition provides a long-lasting treatment effect.

18. A method of treating hair to provide hair benefits selected from the group consisting of bleaching, coloring, conditioning and mixtures thereof by applying to hair an effective amount of composition according to claim 1, wherein the composition provides a long-lasting treatment effect.

19. A treatment composition according to claim 1 wherein the surfactant is a cationic surfactant selected from the group consisting of cetyltrimethylammonium chloride, cetyltrimethylammonium bromide and mixtures thereof.

20. A treatment composition according to claim 1 wherein the ration of cholesterol to cationic surfactant is in a range from about 0.7:1.0 to about 1.25:1.0.

21. A treatment composition according to claim 14 wherein the reactive agent has a cationic charge and the surfactant has a cationic charge.

* * * * *